United States Patent [19]
Allison et al.

[11] 3,945,384
[45] Mar. 23, 1976

[54] ELECTRODE

[75] Inventors: Kenneth C. Allison, Crystal Lake; Howard T. Francis, Park Forest; Robert J. Abele; Kenneth E. Pawlak, both of Chicago, all of Ill.

[73] Assignee: Biomedical International Company, River Grove, Ill.

[22] Filed: Nov. 3, 1972

[21] Appl. No.: 303,335

[52] U.S. Cl. .......................... 128/2.06 E; 128/0.4
[51] Int. Cl.² ................................... D61B 5/04
[58] Field of Search .......... 128/2 E, 2.06 E, 2.1 E, DIG. 4, 417

[56] References Cited
UNITED STATES PATENTS

| 3,590,810 | 7/1971 | Kopecky | 128/2.06 E |
| 3,487,827 | 1/1970 | Edmark | 128/2.06 E |
| 3,587,565 | 6/1971 | Tatoian | 128/2.06 E |
| 2,318,207 | 5/1943 | Ellis | 128/Dig. 4 |
| 3,265,638 | 8/1966 | Goodman et al | 128/417 |
| 3,696,807 | 10/1972 | Szpur | 128/2.1 E |
| 3,610,229 | 10/1971 | Zenkich | 128/2.06 E |
| 3,027,333 | 3/1962 | Friedman | 128/417 |
| 3,659,586 | 5/1972 | Johns et al | 128/2.1 E |

Primary Examiner—William E. Kamm
Attorney, Agent, or Firm—Anthony S. Zummer

[57] ABSTRACT

An electrode for use in cooperation with a signal-receiving apparatus is the subject matter of this invention. The electrode is a disposable electrode which receives a signal from a subject, which signal is then observed. The electrode includes an electrical half cell. The half cell includes a metal portion, which is a terminal of the electrode, and an electrolyte solution. A diaphragm holds the electrolyte solution in contact with the metal. The diaphragm is sufficiently permeable to allow ionic conduction between the surface of the subject and the electrode. A wetting agent in the electrolyte keeps the surface of the diaphragm wetted with electrolyte; and an agent prevents the growth of bacteria. The electrode has a resilient element mounted in the electrolyte in order to urge the diaphragm outwardly. A mounting pad is mounted on the electrode as a portion thereof; and the mounting pad has an adhesive layer on one side for securing the electrode to the subject. An envelope is provided to maintain the electrode in condition ready for use.

17 Claims, 6 Drawing Figures

U.S. Patent   March 23, 1976   3,945,384
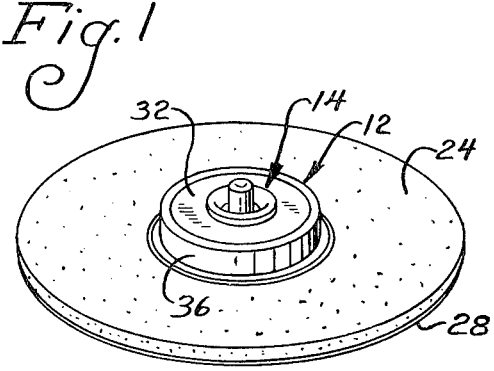
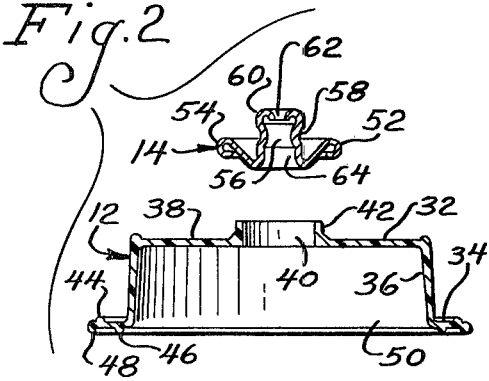
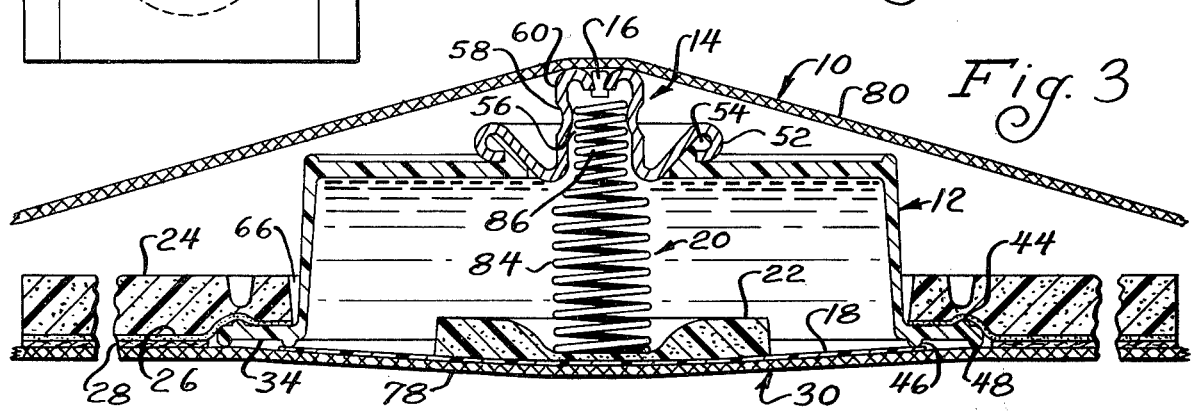
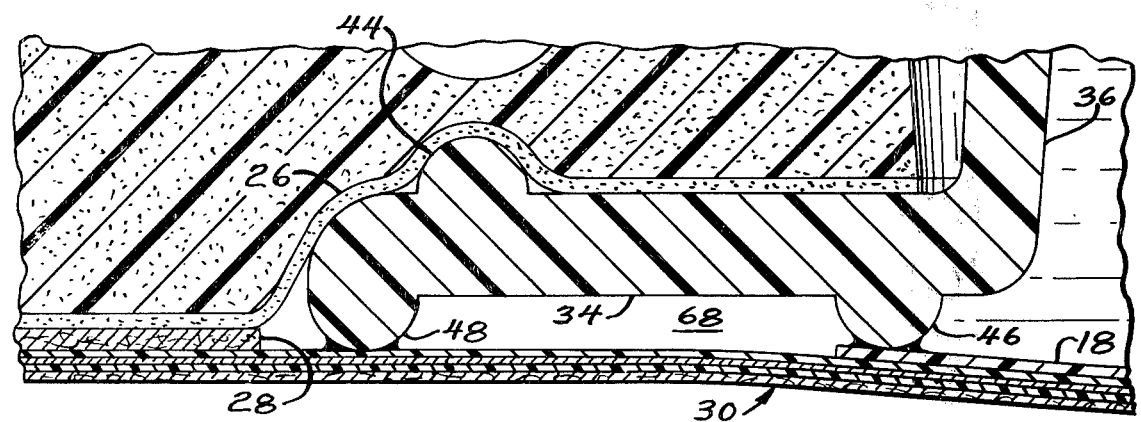

ELECTRODE

BACKGROUND OF THE INVENTION

Electrical measurements are used in monitoring a wide variety of functions. The monitoring of physiological functions, especially those of mammals, has gained wide acceptance in the biomedical area. In order to have a continuous record for certain testing, it is necessary to secure the electrode to a subject for a prolonged period of time. Typical situations in which there is continuous monitoring are; cardiac patients in "intensive care wards of hospitals", astronauts during flights and pre-flight training, and mammals used in closely regulated scientific experiments. These measurements are often used for electrocardiograms, electromyograms, and electroencephalograms, as well as other electrical measurements.

It is recognized that a good electrode has certain important aspects, such as, low impedance and electrical stability. Inasmuch as the electrode operates as a half cell, the half cell potential must be stable. The primary purpose of the electrode is the faithful transmission of signals from a subject to a recording and/or observing apparatus.

A common electrode construction is one which utilizes a silver-silver chloride-chloride ion half cell. The silver-silver chloride-chloride ion half cell is generally formed either by compressing a mixture of silver and silver chloride powders and placing the compressed mixture in contact with a suitable electrolyte, or by forming a half cell by first electrochemically converting the surface of a silver member to a silver chloride layer and placing the silver chloride layer into contact with an electrolyte.

These known electrodes generally have performed satisfactorily in many applications. However, these known electrodes have certain undesirable properties. The electrolyte which is placed in contact with a patient's skin is generally in gel or paste form. The paste is messy to handle, both for the operator and for the patient. The preparation technique causes irritation to the patient, especially when the skin is abraded for a good electrical contact. When prolonged readings are to be taken, the paste tends to dry, causing the impedance to increase at the electrode skin interface, thereby degrading the observed signal and resulting in a failure to make a faithful transmission of the physiologically-generated signal. Furthermore, the electrical characteristics of these electrodes vary from electrode to electrode, and the measurements are limited to use with an AC amplifier. It has also been observed that there are, in certain well-known electrodes, drifts in potential or changes at an erratic rate in relation to time. This drifting causes errors in measurement of signals and thereby gives a distorted view of the physiological signal-generating organ or body portion. A further problem which accompanies certain known electrodes is that the silver chloride cannot be kept in contact with a patient's skin for a prolonged time without causing irriration due to silver migration. When the known electrodes (other than that disclosed in United States Patent Application Serial No. 249,135, filed May 1, 1972, and Serial No. 287,562, filed September 8, 1972) are used on a given patient for a prolonged period, the electrodes are often relocated several times a day, causing discomfort to the patient and affecting the observed signal.

SUMMARY OF THE INVENTION

The present electrode does not require the use of a paste or gel between a surface and the electrode. It is an electrode which establishes a stable half cell potential between a metal and an electrolyte which is an ionic solution. The electrode includes a container for an electrolyte. The container has a permeable membrane on at least one side, which membrane is adapted for engagement with a surface from which an electrical signal is to be observed. The electrode also includes a solid metal, which is in electrochemical equilibrium with the electrolyte. The solid metal is connected to an electrical conductor, which is adapted for connection to an apparatus for observing and/or recording the signal detected at the surface of a subject.

The electrical half cell potential of the electrode is defined by the metal-metal ion interface within the electrode. It is important to note that because this half cell makes electrolytic contact with the surface of the subject under study through the permeable, ion-conductive membrane, the half cell electrolyte is thereby protected against contamination or rapid concentration changes during the period of use of the electrode. Since the potential of the half cell is determined by the choice of solid metal and the ionic solution used as the electrolyte, even violent movements of the subject have no noticeable effect on the readout at the observing and/or recording apparatus. The permeable membrane is in electrical contact with the surface of the subject, so that no paste or gel is required to establish a good contact. The permeable membrane also creates no irritation to the surface of the subject. In addition, as the electrode is used over a prolonged period of time, there may be a certain loss of electrolyte from the electrode by evaporation. The permeable membrane is kept in contact with the surface of the subject by a resilient element mounted within the electrode, which resilient element constantly urges the permeable membrane outward to insure a good contact with the surface of the subject. In order to keep the electrode on a subject without causing irritation, the electrode has as a part of the electrode a pad or backing, which may be porous; and the pad or backing has on one surface a layer of adhesive, which may be porous, so that the electrode may be attached to the surface of the subject and still allow the skin to breathe and normal evaporation to continue, such as from the surface of a mammal. In addition, the construction of the electrode is such that it permits a release paper to be placed on the adhesive surface to make the adhesive surface selectively readily available. The construction of the electrode also allows an envelope to be used in connection with the electrode, that is, the envelope has a portion which is sealed around the diaphragm, thereby completely sealing the electrolyte from the outside and eliminating evaporation. The envelope construction is such that the electrode is completely enclosed to prevent dirt from getting into the electrode. However, the envelope may be readily removed by simply tearing the envelope and peeling the main portion of the electrode off the envelope, thereby exposing the diaphragm and also exposing the release paper, which may be selectively removed.

BRIEF DESCRIPTION OF THE DRAWINGS

FIG. 1 is a perspective view of a portion of an electrode embodying the herein-disclosed invention;

FIG. 2 is an exploded cross-sectional view of a container and terminal of the electrode of FIG. 1;

FIG. 3 is a cross-sectional view of a portion of the electrode of FIG. 1;

FIG. 4 is an enlarged cross-sectional view of a mounting portion of the electrode of FIG. 1;

FIG. 5 is an enlarged fragmentary cross-sectional view of a portion of the envelope of the subject electrode; and FIG. 6 is a plan view of the subject invention.

DESCRIPTION OF THE PREFERRED EMBODIMENT

Referring now to the drawings, and especially to FIG. 3, an electrode which is a specific embodiment of the instant invention is generally indicated by numeral 10. The electrode generally includes a container 12, a terminal 14 mounted on the container, a plug 16 mounted in the terminal, a diaphragm 18 connected to the container 12, a spring 20 mounted in the container 12, and a diaphragm pad 22 positioned between the spring 20 and the diaphragm 18, all of which make up a signal receiver. A mounting pad 24 is connected to the container. The mounting pad has an adhesive layer 26 on one surface, with a release paper 28 adhesively secured to the adhesive 26. An envelope 30 surrounds the container and the mounting pad 24.

The container 12 is injection-molded polypropylene. The container, as it is orginally molded, is shown in FIG. 2. The container, in its original configuration, includes a cup 32, with a mounting flange 34 formed integral with the outer periphery of its open end. The cup includes an annular sloping wall 36, with a top 38 formed integral with the smaller portion of the sloping wall 36. In the center of the top 38, there is an aperture 40 which is surrounded by an upstanding terminal tube 42.

The construction of the flange 34 may be best seen in FIG. 4. The flange 34 is formed integral with the sloping wall 36 of the cup 32. The mounting flange extends radially outward from the center of the cup 32. The mounting flange includes a mounting ridge 44 formed integral with the side of the flange which is toward the top 38. Formed integral with the opposite side of the flange, there is an interior annular diaphragm ridge 46 and a sealing ridge 48 which acts as an envelope mounting ridge. The cup has a mouth 50 which opens into the interior of the cup.

The terminal 14 is a stamped member made of tin-plated brass. The general configuration of the terminal is circular and has a mounting flange 52 at its outer end, with a flange receptacle 54 formed therein. The mounting flange is formed integral with a terminal stud 56. The terminal stud 56 has a necked portion 58 and a head 60 for engagement with an electrical connector. The head 60 includes a filling aperture 62 which extends axially into the terminal stud 56. The interior of the terminal stud forms a spring receptacle 64.

The diaphragm 18 is a permeable membrane which acts as a porous phase separator for the electrode 10. In this instance, the diaphragm is made of conventional polypropylene material. The edges of the diaphragm are sealingly attached to the diaphragm ridge 46, as may be best seen in FIGS. 3 and 4.

The mounting pad 24 is a reticulated foam of polyurethane in which there are 100 pores per linear inch. The mounting pad has a cup aperture 66 in its central portion to receive the cup 32. The mounting pad is secured to the mounting flange 34 at the mounting ridge 44. The adhesive layer 26 also engages the mounting flange in order to further secure the mounting pad to the container. A conventional release paper 28 having an aperture 68 to receive the container engages the adhesive 26 and may be peeled off the adhesive.

The coil spring 20 is made of brass having 70% copper and 30% zinc, and is tin-plated. The coil spring 20 includes a main body 84 and a terminal neck 86 which is formed integral with the main body 84. The terminal neck 86 is positioned in the spring receptacle 64 of the terminal 14, as may be best seen in FIG. 3. Mounted below the spring 20 and in contact with the diaphragm 18 is a spring pad 22. The spring pad is also polyurethane and has a porosity in the range of 10 to 40 pores per inch. The general construction of the spring pad 22 is circular and extends laterally outward along the interior surface of the diaphragm 18, as is best shown in FIG. 3. The pad performs a dual function. One is to protect the diaphragm from the spring 20; and the second is to maintain an electrolyte in contact with the spring.

The electrolyte, in this instance, is an 0.25% sodium chloride solution. In addition to the sodium chloride, there is in the electrolyte a surface active agent (in this instance, Polysorbate 80 U.S.P.) in the concentration of 0.25%. In addition, there is also contained in the electrolyte an agent to prevent the growth of bacteria, which in this instance is a quaternary ammonium compound.

The envelope 30 is made of sheet material having four-plys. The outermost ply, as shown in FIG. 5, is a paper sheet 70. Secured to the paper sheet 70 is a ply of sheet polyethylene 72. An aluminum foil sheet 74 is in engagement with the polyethylene 72, and a sheet of ethylene vinyl acetate copolymer 76 is the innermost layer of material. The sheet material is placed into engagement with the sealing ridge 48, so that the ethylene vinyl acetate copolymer sheet 76 is sealingly and releasably engageable with the ridge 48. The envelope is constructed in a manner so that one-half of the envelope is placed under the electrode main body. The remainder of the envelope is folded over the top of the electrode so that a lower sheet 78 is engagement with the bottom of the container; and an upper sheet 80, which is formed integral with the lower sheet, engages the terminal 14. The three open sides of the envelope are sealed by making a seal 82 adjacent to each of the sides, as shown in FIG. 6, thereby completely enclosing the main portion of the electrode.

It may be appreciated that the instant electrode may be readily and conveniently assembled. The container is injection-molded, with the terminal tube 42 formed integral therewith. As was mentioned above, the terminal 14 is stamped out. In order to assemble the terminal 14 to the container 12, the terminal tube 42 and the terminal flange 52 are heated; and the terminal is pressed onto the container so that the terminal tube 42 of the container flows up along the mounting flange of the terminal and into the flange receptacle 54. When the material cools, the terminal is securely attached to the container. The spring 20 is placed into position, with the neck 86 in the spring receptacle 64. The pad 22 is placed into position; and the diaphragm 18 is then placed over the pad, with the spring being slightly compressed. The diaphragm and the ridge 46 are heated at the portion where the diaphragm contacts the ridge 46 to seal the diaphragm to the container and thereby form an enclosed cavity.

The mounting pad 24 is cut to size; and the adhesive layer 26 is applied to mounting pad 24. The release paper 28, having been cut to size, is also applied to the adhesive layer; and the mounting pad is then attached to the mounting flange 34 of the container. A heated circular tool is used to apply heat to the mounting pad at the mounting ridge 44 to heat the material of the mounting pad and to secure the mounting pad to the mounting ridge 44. The electrolyte is added to the interior of the container with a vacuum process, that is, the air from the cavity formed by the container and the diaphragm is evacuated while the electrolyte is inserted through the filling aperture 62 to fill the cavity. The filling aperture 62 is then sealed closed with the plug 16.

The envelope 30 is then attached by placing the container on the bottom sheet 78 and applying heat to the point where the ethylene vinyl acetate copolymer touches the sealing ridge so that the copolymer is in actual sealing engagement with the ridge and seals off the entire outer surface of the diaphragm 18. The top sheet 80 is folded over; and the seals 82 are then made to completely enclose the envelope.

It may be appreciated that, in the envelope, the present electrode has an extremely long shelf life in view of the fact that there is no loss of water from the electrode due to evaporation since the electrode is completely encased in its envelope. The electrolyte is further contained in the container by the seal of the bottom sheet 78 to the ridge 48. In order to use the electrode, the operator need only tear the envelope and then pull the bottom sheet 78 off the sealing ridge 48, thereby exposing the diaphragm 18. The operator then simply peels off the release paper 28, exposing the adhesive layer 26. The electrode is now ready for use. The operator applies the electrode to the required area on the subject; and the electrode is adhesively secured to the subject. The subject does not suffer any discomfort on the surface area in view of the fact that the mounting pad 24 is porous, as is the adhesive layer 26, as mentioned before. It is important to note that the operator need not apply any paste or gel to the skin of a patient; and the electrode may stay on the patient's skin for a prolonged period of time. The spring 20, which acts as a resilient element, keeps the diaphragm in contact with the skin of a patient to maintain electrolytic contact. As is well-known, the instant half cell reaction is a tin-tin ion half cell reaction. The electrode faithfully transmits signals from the surface under observation because the tin and tin ion concentrations are essentially constant during the period of use; therefore, the electrode is insensitive to motion.

From the foregoing description, it may be readily seen that the instant electrode may be readily and quickly assembled; and it may be easily used by an operator. Although a specific embodiment of the herein-disclosed invention has been shown and described in detail above, it is to be understood that the instant invention is limited only by the appended claims.

What is claimed is:

1. A biomedical electrode for use on a subject to take electrical measurements from said subject comprising, a solid metal being adapted for being electrically connected to an instrument for making electrical measurements, an ionic solution in contact with the solid metal, means for holding the ionic solution in contact with the solid metal, said means including a porous phase separator having one side contacting the ionic solution and the other side being adapted for direct contact with a surface of the subject, said porous phase separator being wettable by the ionic solution to wet said other side for ionic conduction between the surface and the ionic solution through the phase separator, and resilient means connected to said one side of the porous phase separator contacting the ionic solution for urging the porous phase separator outward from the ionic solution.

2. A biomedical electrode for use on a subject to take electrical measurements from said subject as defined in claim 1, including a pad positioned between the resilient means and the one side of the porous phase separator contacting the ionic solution, said pad extending laterally along said one side to distribute the force of the resilient means along said one side.

3. A biomedical electrode for use on a subject to take electrical measurements from said subject as defined in claim 1, including a waterproof envelope surrounding the means for holding the ionic solution and the porous phase separator.

4. A biomedical electrode for use on a subject to take electrical measurements from said subject comprising, a container comprising a cup having a flange formed integral with the outer periphery of the open side of the cup and an aperture contained in said cup, a metal terminal mounted in the aperture in the cup for closing the aperture and being adapted for electrical connection to an instrument for making electrical measurements, a permeable diaphragm sealingly secured to the flange for closing the open side of the cup, and an electrolyte in the cup permeating said diaphragm to wet the side of the diaphragm away from the cup, said diaphragm being adapted for direct contact with a surface of a subject for ionic conduction between the surface and the electrolyte.

5. A biomedical electrode for use on a subject to take electrical measurements from said subject as defined in claim 4, including an open-cell porous pad secured to the flange, an adhesive layer on the side of the pad adjacent to the diaphragm, and a release sheet mounted on the adhesive layer.

6. A biomedical electrode for use on a subject to take electrical measurements from said subject as defined in claim 5 wherein the adhesive layer is porous.

7. A biomedical electrode for use on a subject to take electrical measurements from said subject as defined in claim 5, including resilient means mounted in the cup and connected to the interior surface of the diaphragm for urging the diaphragm outward from the cup.

8. A biomedical electrode for use on a subject to take electrical measurements from said subject as defined in claim 7 wherein the resilient means is a metal spring being in electrical contact with the terminal.

9. A biomedical electrode for use on a subject to take electrical measurements from said subject as defined in calim 8, including a pad positioned between the end of the spring and the diaphragm to distribute the force of the spring on the diaphragm.

10. A biomedical electrode for use on a subject to take electrical measurements from said subject as defined in claim 4, including resilient means mounted in the cup and being connected to the interior surface of the diaphragm to urge the diaphragm outwardly from the cup.

11. A biomedical electrode for use on a subject to take electrical measurements from said subject as defined in claim 10, including a pad positioned between resilitent means and the diaphragm, said pad extending laterally along said diaphragm to distribute the forces of the resilient means on the interior surface of the diaphragm.

12. A biomedical electrode for use on a subject to take electrical measurements from said subject comprising, a container having an open side, a permeable diaphragm sealingly secured to the container closing said open side, a pad connected to the container and having one side being positionable in substantially the same plane as the diaphragm, an adhesive mounted on one side of the pad being in substantially the same plane as the diaphragm, an electrolyte in said container permeating said diaphragm to wet the side of the diaphragm away from the container, said diaphragm being adapted for direct contact with a surface of a subject for ionic conduction between the surface and the electrolyte, and a metal contacting the electrolyte and being adapted for connection to an instrument for making electrical measurements.

13. A biomedical electrode for use on a subject to take electrical measurements from said subject as defined in claim 12, including a closed envelope surrounding the container, said envelope having a portion sealingly connected to the container and surrounding said diaphragm to seal closed releasably the diaphragm.

14. A biomedical electrode for use on a subject to take electrical measurements from said subject as defined in claim 13, including resilient means mounted in the container and being connected to the interior surface of the diaphragm to urge the diaphragm outwardly from the container.

15. A biomedical electrode for use on a subject to take electrical measurements from said subject as defined in claim 12, including a wetting agent in the electrolyte for wetting the surface of the diaphragm.

16. A biomedical electrode for use on a subject to take electrical measurements from said subject as defined in claim 12 wherein said metal being a metal terminal having a filling aperture permanently in its central portion, and a plug mounted in said filling aperture sealingly closing the aperture.

17. A biomedical electrode for use on a subject to take electrical measurements from said subject as defined in claim 12, including resilient means connected to the interior side of the diaphragm for urging the diaphragm outward from the container.

* * * * *